United States Patent
Nichol et al.

(10) Patent No.: US 6,620,913 B1
(45) Date of Patent: Sep. 16, 2003

(54) POLYPEPTIDES OF A NOVEL HANTAVIRUS

(75) Inventors: Stuart T. Nichol, Atlanta, GA (US); Christina F. Spiropoulou, Atlanta, GA (US); Thomas G. Ksiazek, Lilburn, GA (US); Pierre E. Rollin, Lilburn, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/125,631

(22) Filed: Apr. 18, 2002

Related U.S. Application Data

(63) Continuation of application No. 09/669,024, filed on Sep. 25, 2000, now abandoned, which is a continuation of application No. 08/084,724, filed on Jun. 24, 1993, now abandoned.

(51) Int. Cl.[7] .................... C07K 1/00; C07K 14/00; C07K 17/00
(52) U.S. Cl. ...................................... 530/350
(58) Field of Search ........................ 530/350

(56) References Cited

PUBLICATIONS

Sommer and Tautz, "Minimal homology requirements for PCR primers," Nucleic Acids Research 17(16):6749 (1989). Sequence Comparison # 6 pp. 24–25.

Antic et al., "Comparison of the deduced gene products of the L, M, and S genome segments of hantaviruses," Virus Res. 24:35–46 (1992).

CDC, "Outbreak of acute illness–Southwestern United States, 1993" Morbidity and Mortality Weekly Report 42:421–424 (Jun. 11, 1993).

CDC, "Outbreak of acute illness–Southwestern United States, 1993" Morbidity and Mortality Weekly Report 42:477–479 (Jun. 25, 1993).

CDC, "Outbreak of acute illness–Southwestern United States, 1993" Morbidity and Mortality Weekly Report 42:495–496 (Jul. 2, 1993).

CDC, "Outbreak of acute illness–Southwestern United States, 1993" Morbidity and Mortality Weekly Report 42:570–571 (Jul. 30, 1993).

CDC, "Outbreak of acute illness–Southwestern United States, 1993" Morbidity and Mortality Weekly Report 42:612–614 (Aug. 13, 1993).

Elliott et al., "Nucleotide Sequence and Expression of the Small (S) RNA Segment of Maguari Bunyavirus," Virology, 171:516–524 (1989).

Kallio–Kokko et al., "Puumala virus Antibody and Immunoglobulin G Avidity Assays Based on a Recombinant Nucleocapsid Antigen," Journal of Clinical Microbiology 31:368–372 (Mar., 1993).

Lundkvist et al., "Immunoglobulin G Subclass Responses against the Structural Components of Puumala Virus," Journal of Clinical Microbiology 31:368–372 (Feb. 1993).

Yoo, et al., "Genomic comparison among members of Hantavirus group," In The Biology of Negative Strand Virus, Mahy & Kolakofsky (Eds.), Elsvier Science Publishers BV (1987).

CDC, "Update: Outbreak of acute illness—Southwestern United States, 1993," *Morbidity and Mortality Weekly Report* 42:441–443 (Jun. 18, 1993).

Schmaljohn and Patterson in Fundamental Virology, 2nd Ed., "Bunyaviridae and Their Replication" pp. 545–564 (1991).

Plummer et al. People Weekly, 30–33 (Jun. 21, 1993).

*Primary Examiner*—James Ketter
*Assistant Examiner*—Konstantina Katcheves
(74) *Attorney, Agent, or Firm*—Needle & Rosenberg, P.C.

(57) ABSTRACT

The present invention relates to the discovery of a novel Hantavirus. In particular, the present invention relates to nucleic acids of the newly discovered virus and to nucleic acid reagents and antibodies for use in methods of detection and prevention of infection by the virus.

2 Claims, No Drawings

SEQUENCE LISTING

```
<160> NUMBER OF SEQ ID NOS: 2

<210> SEQ ID NO 1
<211> LENGTH: 562
<212> TYPE: DNA
<213> ORGANISM: Artificial Sequence
<220> FEATURE:
<223> OTHER INFORMATION: Description of Artificial Sequence; Note =
      Synthetic Construct
```

```
<400> SEQUENCE: 1
gactaaagct ggaatgagca ccctcaaaga agtgcaagac aacatcactc tccacgaaca    60
acaactcgtg actgccaggc agaagctcaa agatgcagaa agagcggtgg aattggaccc   120
cgatgatgtt aacaaaagca cattacagag cagacgggca gctgtgtctg cattggagac   180
caaactcgga gaacttaagc gggaactggc tgatcttatt gcagctcaga aattggcttc   240
aaaacctgtt gatccaacag ggattgaacc tgatgaccat ctaaaggaaa agtcatcatt   300
gagatatgga aatgtccttg atgtaaattc cattgactta aagagccaa gtgggcaaac   360
agctgattgg aaatccatcg gactctacat tctaagtttc gcattaccga ttattcttaa   420
agccttgtac atgttatcta ctaggggccg tcaaacaatc aaagaaaaca agggaacaag   480
aattcgattc aaggatgatt catcttatga agaagtcaat gggatacgta agccaagaca   540
tctgtatgtt tctatgccaa ct                                            562

<210> SEQ ID NO 2
<211> LENGTH: 911
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 2
tacgacacca acatgtgagt atcaaggcaa cacagtgtct ggattccaac gcatgatggc    60
aactcgagat tctttccagt cattcaatgt gacagaacca catatcacta gcaaccgact   120
tgagtggatt gatccagata gcagtatcaa agatcacatt aatatggttt taaatcgaga   180
tgtttccttt caggatctaa gtgataaccc atgcaaggtt gacctgcata cacaatcaat   240
tgacggggcc tggggttcag gagtaggttt tacgttggta tgtactgtgg ggcttacaga   300
gtgtgcaaat tttataactt caattaaagc atgtgattct gccatgtgtt atggagccac   360
agtgacaaat ctgctagag ggtctaacac agttaaagtt gttggtaaag gtgggcattc   420
tggatctttg tttaaatgct gccatgatac tgactgtacc gaagaagggt tagcagcatc   480
tccaccacat ttagacaggg ttacaggcta taatcaaata gattctgatt aaagtttatg   540
atgacggtgc accgcctgta caatcaagtg ctggttcacc aagtcaggtg aatggctgtt   600
gggaatcctt aatggcaatt gggtggtagt tgctgttctg attgtaattt tgatattatc   660
gatactcctt tttagctttt tttgtcctgt cagaagtaga aagaataaag ctaattagtg   720
aatatatatg tgagcaagag tatgacaaca ttatttcatt atatgtatgt tcttatatca   780
ataacatttg tatattccca taaccgaaat atttatacta attttattt ttaaacaagt   840
attaactaac ccattaacag ctaaaaaaaa caaatcctta acacctatat aatcccattt   900
gcttattacg a                                                        911
```

POLYPEPTIDES OF A NOVEL HANTAVIRUS

BACKGROUND OF THE INVENTION

The present application is a 37 C.F.R. § 1.53(b) continuation patent application of U.S. Utility application Ser. No. 09/669,024, filed Sep. 25, 2000 now abandoned which is a continuation patent application of U.S. Utility application Ser. No. 08/084,724, filed Jun. 24, 1993, now abandoned which is incorporated herein in its entirety by reference.

FIELD OF THE INVENTION

The present invention relates to discovery of a novel Hantavirus. In particular, the present invention relates to nucleic acids of the novel Hantavirus and to nucleic acid reagents and antibodies for use in methods of detection and prevention of infection by the new virus.

BACKGROUND ART

Recently, an outbreak of an unknown disease presenting with the abrupt onset of fever, myalgia, headache, cough and finally respiratory failure occurred in the Four Corners Region of the United States. The disease has been clinically termed ARDS (unexplained Adult Respiratory Distress Syndrome). Of the 12 human cases that have been reported, 75% of these patients have died. The outbreak appears to be confined primarily to the Four Corners Region of New Mexico, Arizona and Colorado.

The high mortality associated with ARDS and the unknown etiology of the pathogen created an urgent need to isolate and identify the pathogen and to provide reliable methods for diagnosis, treatment and prevention of the disease. The present invention satisfied that need by identifying a previously unreported strain of Hantavirus as the causative agent of the ARDS outbreak. The present invention also provides methods to diagnose and prevent infection.

SUMMARY OF THE INVENTION

The present invention provides the discovery and isolation of a new virus. This virus is the etiologic agent responsible for the outbreak of the Adult Respiratory Distress Syndrome (ARDS) in the Four Corners Region of the United States. Based upon genetic characteristics, this new virus should be classified in the Hantavirus family.

The present invention also provides isolated nucleic acids and nucleic acid reagents which can be utilized to diagnose and prevent infection of the new virus. Purified polypeptides encoded by the nucleic acids are also provided. These polypeptides can be utilized in methods of diagnosis or as vaccine components for prevention of infection.

Vectors are also provided which comprise the nucleic acids of the present invention. The vectors can be utilized in host expression systems to produce antigenic peptide reagents for diagnostic and prophylactic applications.

The present invention also provides purified antibodies selectively reactive with the new virus of the invention. These antibodies can be used in various diagnostic methods or as a therapeutic.

DESCRIPTION OF THE EMBODIMENTS

The present invention may be understood more readily by reference to the following detailed description of specific embodiments and the examples included therein.

As used in the claims, "a" can mean one or more.

Virus Characterization

In general, Hantaviruses are spherical 28-nm viruses that were initially identified from the feces of rodents. They have distinctive ultrastructural glycoprotein surfaces of 5–10 nm that are embedded in a lipid bi-layered envelope. The negative sensed RNA of the viral genome consists of three fragments generally designated as S, M, and L for the small, medium, and large genome fragments respectively. The S segment encodes a nucleocapsid protein, where as the M segment encodes the surface glycoproteins G1 and G2. (Schmaljohn, C. S. et al., *Fund. Virol.*, 545:545 (1991)). Four types of Hantavirus have been previously identified and are currently designated Hantaan, Seoul, Puumala, and Prospect Hill Virus. Infection with these agents is usually contracted through contact with the feces and urine of infected rodents.

The discovery of the new virus of the present invention arose out of attempts to identify the etiologic agent responsible for the ARDS outbreak. Antibodies to hundreds of potential bacterial and viral pathogens were screened before a weak serologic cross reactivity was detected. Early results of immunological screening (IFA and IgM and IgG ELISA tests) of sera from case-patients suggested the possible involvement of a Hantavirus in this disease outbreak. This was based on limited immune cross-reactivity of sera with known Hantavirus antigens. Using this information, a genetic approach was developed to attempt to identify this virus.

By retrieving the nucleotide sequences of the known Hantaviruses from the GENBANK database and aligning these sequences with one another, we were able to identify regions of shared sequence similarity between these viruses. Oligonucleotide primers targeting these regions of sequence conservation were designed to provide two independent, nested Polymerase Chain Reaction (PCR) assays for the detection of virus RNA, one targeting Hantaan/Seoul-like virus RNA and the other Puumala/Prospect Hill-like virus RNA. Each assay involves two sets of primers. The first reaction utilizes the enzymes reverse transcriptase and Taq polymerase together with plus sense and minus sense virus-specific primers to synthesize a cDNA copy of target viral RNA and then greatly amplify the quantity of these DNA molecules. Utilizing a second pair of primers, the DNA products of the first reaction are further amplified in a second PCR reaction. This greatly increases both the sensitivity and specificity of this detection assay.

Total RNA was extracted from autopsy tissues taken from numerous cases thought to be associated with the Four Corners disease outbreak. Positive PCR bands of the correct size were obtained in the second round reaction with the Puumala/Prospect Hill designed primers with RNA extracted from tissues from three individuals. Direct sequence analysis of these PCR DNA products revealed the presence of a previously unrecognized Hantavirus in these individuals. Genetic sequence comparisons demonstrated that this virus differed from any previously characterized Hantavirus by more than approximately 30%.

Specifically, the nucleic acid sequences of the new virus shown in SEQ ID NO:1 and SEQ ID NO:2 were compared to the genomic segments from the known types of Hantavirus, i.e., Prospect Hill, Puumula, Hantaan, and Seoul. Prospect Hill virus showed approximately a 70% sequence homology to the new virus. Homology with Puumula was about 69% and about 61% with the Hantaan and Seoul viruses.

A comparison of these findings with the sequence homology that exists between the known Hantavirus types is as follows: Prospect Hill:Puumula is about 70%; Prospect Hill:Hantaan is about 58%; and Prospect Hill:Seoul is about 58%. These data clearly indicate that the virus discovered by the present invention is a new Hantavirus type.

Genetically highly similar viral sequences were PCR amplified from tissue samples taken from Peromyscus spp. rodents trapped in the Four Corners area, suggesting a direct genetic link between the virus in rodents and in clinical cases. Up to 7% nucleotide sequence differences were seen among PCR products from different human cases associated with the Four Corners region outbreak. However, identical viral sequences were consistently obtained for specific individual cases, independent of tissue source or RNA sample preparation, i.e., the sequence variation was not an artifact of the PCR or sequencing methods employed. This level of genetic variation is not uncommon for RNA viruses. We predict that up to approximately 15% nucleotide sequence deviation from the consensus sequence of this newly identified hantavirus can be reasonably expected. Thus, typically genetic variants of the new virus will be greater than 80% homologous, especially greater than about 15% or 10% homologous. To date, the greatest degree of variance between field isolates of the new virus from the current outbreak is about 7%.

The clinical signs and pathology associated with the new virus are also surprisingly different from that of other Hantaviral infections which usually present as an acute hemorrhagic fever with renal syndrome. The ARDS viral agent identified by the present invention instead produced acute respiratory failure and high mortality in young adults.

The present invention provides an isolated virus comprising the nucleotide sequence set forth in the Sequence Listings as SEQ ID NO:1 and SEQ ID NO:2, or genetic variants thereof. By "isolated virus" is meant the virus has been separated from the tissue contaminants with which the virus naturally occurs. By "genetic variants" is meant a virus having sufficient homology to the virus identified by SEQ ID NO:1 and SEQ ID NO:2, such that primers and probes made from the sequences of the genetic variant will selectively hybridize with the virus identified by SEQ ID NO:1 and SEQ ID NO:2. By "selectively hybridize" is meant the nucleic acid does not hybridize with sequences from previously existing hantavirus to prevent an adequate positive hybridization with the virus identified by SEQ ID NO:1 and SEQ ID NO:2. The virus identified by SEQ ID NO:1 and SEQ ID NO:2 is alternatively referred to herein as "the new virus."

Virus Isolation

Briefly, the new Hantavirus of the present invention can be isolated as follows: The materials suspected of containing the virus are ground in sterile tissue culture medium with a mortar and pestle and sterile powdered glass. The suspension is then allowed to adsorb onto cells, e.g., Vero-E6, MA-104, HMEC-1, or other microvascular or large vessel endothelial cell line for 1 or 2 hours and maintenance medium (MEME with 2% heat inactivated FBS) is added and changed every 5 or 7 days. Periodically, the cells are scraped with a rubber policeman or trypsinized from the plastic and dried onto glass slides for fixation and observation by indirect fluorescent antibody microscopy for hantaviral antigens using polyclonal and monoclonal antibodies. The cells are subpassaged every two weeks and allowed to grow to confluence. The material is carried for a minimum of 5 subpassages (6 total passages) before it is considered negative.

Rodents for isolation attempts can be identified by testing blood from individuals and then attempting isolation on the lungs or kidneys (as outlined above) of those rodents found to have antibodies. Rodents are considered good sources for Hantavirus because the rodents are chronically or persistently infected with the virus.

Animal inoculation can also be utilized for viral isolation. In this instance, suckling ICR mice have been inoculated (intracranially and intraperitoneally), Guinea pigs (intraperitoneally) and Mongolian gerbils (intraperitoneally). The tissues are being blind passaged in the rodents and the tissues tested for the presence of Hantavirus antigens and nucleic acids.

Nucleic Acids

The present invention provides an isolated nucleic acid comprising the nucleotide sequence set forth in the Sequence Listing as SEQ ID NO: 1, or a sequence complementary thereto. The RNA sequence shown in SEQ ID NO:1 is a 562 bp segment derived from the S segment of the new virus of the present invention.

By "isolated nucleic acid" is meant separated from other nucleic acids found in the naturally occurring organism. The nucleic acids of the present invention can include positive and negative strand RNA as well as DNA and is meant to include genomic and subgenomic nucleic ac ids found in the naturally occurring organism. The nucleic acids contemplated by the present invention include negative stranded vRNA of the genome, complementary positive stranded cRNA and mRNA, and complementary cDNA produced therefrom and any nucleic acid which can hybridize to or encode the new virus. The nucleic acids of the present invention specifically include RNA from the three genome segments designated small (S), medium (M) and large (L) and nucleic acids complementary thereto.

The present invention also provides an isolated nucleic acid comprising the nucleotide sequence set forth in the Sequence Listings as SEQ ID NO: 2, or a sequence complementary thereto. The RNA sequence shown in SEQ ID NO:2 is a 911 bp segment derived from the M segment of the new virus of the present invention.

The present invention also provides an isolated nucleic acid that is capable of selectively hybridizing with the nucleic acid comprising the nucleotide sequence set forth in the Sequence Listings as SEQ ID NO:1, or a sequence complementary thereto. The present invention also provides an isolated nucleic acid that is capable of selectively hybridizing with the nucleic acid comprising the nucleotide sequence set forth in the Sequence Listings as SEQ ID NO:2, or a sequence complementary thereto. Thus, an isolated nucleic acid capable of selectively hybridizing with or selectively amplifying all regions of the genome of the new virus of the present invention is contemplated. The sequences can be selected based a nucleotide sequence comparison with presently known Hantavirus. Available computer programs can be used to compare the sequence to select the most appropriate sequences for hybridization or amplification.

Modifications to the nucleic acids of the invention are also contemplated as long as the essential structure and function of the polypeptide encoded by the nucleic acids is maintained. Likewise, fragments used as primers or probes can have substitutions so long as enough complementary bases exist for selective hybridization (Kunkel et al., *Methods Enzymol.* 154:367 (1987)).

The nucleic acids described herein can be used to detect the new virus of the present invention in methods such as the polymerase chain reaction, ligase chain reaction, hybridization and the like. Alternatively, these sequences can be utilized to produce an antigenic protein or protein fragment.

In addition, fragments of the nucleic acids described herein can be selected to be homologous with nucleotide sequences present in other human or animal Hantaviruses. Such an nucleotide sequence shared with other Hantaviruses can be used for example to simultaneously detect related strains or as a basis for a multiprotective vaccine.

Nucleic Acid Detection (Diagnosis) Methods

The presence of the new virus described herein can also be determined by detecting the presence of a nucleic acid specific for the new virus as described above and as follows. The present invention provides reagents which can be used in a method of detecting the presence of the new virus in a subject, comprising detecting the presence of the nucleic acid encoding the new virus. The specificity of these sequences for the new virus can be determined by conducting a computerized comparison with known sequences, catalogued in GenBank, a computerized database, using the computer programs Word Search or FASTA of the Genetics Computer Group (Madison, Wis.), which search the catalogued nucleotide sequences for similarities to the nucleic acid in question.

The nucleic acid specific for the new virus can be detected utilizing a nucleic acid amplification technique, such as polymerase chain reaction (PCR) or ligase chain reaction (LCR). Alternatively, the nucleic acid is detected utilizing direct hybridization or by utilizing a restriction fragment length polymorphism. For example, the present invention contemplates a method of detecting the presence of the new virus comprising ascertaining the presence of a nucleotide sequence associated with a restriction endonuclease cleavage site. In addition, PCR primers which hybridize only with nucleic acids specific for the new virus can be utilized. The presence of amplification indicates the presence of the virus. In another embodiment a restriction fragment of a nucleic acid sample can be sequenced directly using, techniques known in the art and described herein and compared to the known unique sequence to detect the new virus. The present invention also contemplates a method of detecting the presence of the new virus by selective amplification by the methods described herein. Alternatively, the new virus can be detected by directly hybridizing the unique sequence with a nucleic acid probe selective for the new virus. Furthermore, the nucleotide sequence could be amplified prior to hybridization by the methods described above.

Alternative probing techniques, such as LCR, involve the use of mismatch probes, i.e., probes which are fully complementary with the target except at the point of the mutation. The target sequence is then allowed to hybridize both with oligonucleotides which are fully complementary and have oligonucleotides containing a mismatch, under conditions which will distinguish between the two. By manipulating the reaction conditions, it is possible to obtain hybridization only where there is full complementarity. If a mismatch is present there is significantly reduced hybridization.

The polymerase chain reaction (PCR) and reverse transcriptase PCR are techniques that amplify specific nucleic acid sequences with remarkable efficiency. Repeated cycles of denaturation, primer annealing and extension carried out with polymerase, e.g., a heat stable enzyme Taq polymerase, leads to exponential increases in the concentration of desired nucleic acid sequences. Given a knowledge of the nucleotide sequence of the new virus as provided herein, synthetic oligonucleotide can be prepared which are complementary to sequences which flank the nucleic acid of interest. Each oligonucleotide is complementary to one of the two strands. The nucleic acid can be denatured at high temperatures (e.g., 95° C.) and then reannealed in the presence of a large molar excess of oligonucleotide. The oligonucleotide, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a nucleic acid segment by more than one million-fold can be achieved. The resulting nucleic acid may then be directly sequenced in order to locate any genetic alteration.

In yet another method, PCR may be followed by restriction endonuclease digestion with subsequent analysis of the resultant products. Nucleotide substitutions can result in the gain or loss of specific restriction endonuclease site. The gain or loss of a restriction endonuclease recognition site facilitates the detection of the organism using restriction fragment length polymorphism (RFLP) analysis or by detection of the presence or absence of a polymorphic restriction endonuclease site in a PCR product that spans the sequence of interest.

For RFLP analysis, RNA is obtained, for example from a tissue sample, blood, gastric specimen, saliva, dental plaque, other bodily fluids of the subject suspected of containing the new virus. DNA amplified from the RNA is digested with a restriction endonuclease, and subsequently separated on the basis of size by agarose gel electrophoresis. The Southern blot technique can then be used to detect, by hybridization with labeled probes, the products of endonuclease digestion. The patterns obtained from the Southern blot can then be compared. Using such an approach, the nucleic acid of the new virus is detected by determining the number of bands detected and comparing this number to the number seen with nucleic acid from the new virus.

Similar creation of additional restriction sites by nucleotide substitutions at the disclosed mutation sites can be readily calculated by reference to the genetic code and a list of nucleotide sequences recognized by restriction endonucleases. Single strand conformational analysis (SSCA) offers a relatively quick method of detecting sequence changes which may be appropriate in at least some instances.

In general, primers for PCR and LCR are usually about 20 bp in length and the preferable range is from 15–25 bp. Better amplification is obtained when both primers are the same length and with roughly the same nucleotide composition. Denaturation of strands usually takes place at 94° C. and extension from the primers is usually at 72° C. The annealing temperature varies according to the sequence under investigation. Examples of reaction times are: 20 mins denaturing; 35 cycles of 2 min, 1 min, 1 min for annealing, extension and denaturation; and finally, a 5 min extension step.

Antigen

Purified antigenic polypeptides, or antigenic fragments thereof, encoded by the nucleic acids of the present invention are also contemplated. As used herein, "encoded" is meant to include negative stranded genomic vRNA capable of transcription into positive strand cRNA or mRNA and includes the viral polypeptides specifically encoded by positive sense cRNA or mRNA produced synthetically or found in the naturally occurring organism. As used herein, "purified" means the antigen is sufficiently free of contaminants or cell components with which the antigen normally occurs to distinguish the antigen from the contaminants or components. Purified antigen from the new virus of the present invention and antigenic fragments thereof are also referred to herein as "the antigen" or "the antigen of the new virus."

In one embodiment, the present invention provides a purified polypeptide comprising the amino acids encoded by the nucleic acids of the invention. Such nucleic acids include those capable of selectively hybridizing with the nucleotide sequence set forth in the Sequence Listings as SEQ ID NO:1 or SEQ ID NO:2, or a sequence complementary thereto.

Naturally, relevant polypeptides are only those encoded by the plus strands. The purified polypeptides can be tested to determine their antigenicity and specificity by the methods taught herein. Antigenic fragments of the antigen can also be synthesized directly or obtained by chemical or mechanical disruption of the virus or larger polypeptides. An immunoreactive fragment is defined as an amino acid sequence of at least about 5 consecutive amino acids derived from the amino acid sequence.

The polypeptide fragments of the present invention can also be recombinant proteins obtained by cloning nucleic acids encoding the polypeptide in an expression system capable of producing the antigenic polypeptide or fragments thereof.

Once the amino acid sequence of the antigen is provided, it is also possible to synthesize, using standard peptide synthesis techniques, peptide fragments chosen to be homologous to immunoreactive regions of the antigen and to modify these fragments by inclusion, deletion or modification of particular amino acids residues in the derived sequences. Thus, synthesis or purification of an extremely large number of peptides derived from the antigen is possible.

The amino acid sequences of the present polypeptides can contain an immunoreactive portion of the antigen attached to sequences designed to provide for some additional property, such as solubility. The amino acid sequences of the polypeptides can also include sequences in which one or more amino acids have been substituted with another amino acid to provide for some additional property, such as to remove/add amino acids capable of disulfide bonding, to increase its bio-longevity, alter enzymatic activity, or alter interactions with gastric acidity. In any case, the peptide must posses a bioactive property, such as immunoreactivity, immunogenicity, etc.

Determining Immunogenicity

The purified polypeptide fragments thus obtained can be tested to determine their immunogenicity and specificity. Briefly, various concentrations of a putative immunogenically specific fragment are prepared and administered to an animal and the immunological response (e.g., the production of antibodies or cell mediated immunity) of an animal to each concentration is determined. The amounts of antigen administered depend on the subject, e.g. a human or a guinea pig, the condition of the subject, the size of the subject, etc. Thereafter an animal so inoculated with the antigen can be exposed to the virus to test the potential vaccine effect of the specific immunogenic fragment. The specificity of a putative immunogenic fragment can be ascertained by testing sera, other fluids or lymphocytes from the inoculated animal for cross reactivity with other closely related Hantaviruses.

Vectors and Hosts

A vector comprising the nucleic acids of the present invention is also provided. The vectors of the invention can be in a host capable of expressing the antigenic polypeptide fragments contemplated by the present invention.

In one embodiment, the present invention provides a vector comprising a nucleic acid complementary to or capable of selectively hybridizing with nucleic acid comprising the nucleotide sequence set forth in the Sequence Listings as SEQ ID NO: 1, or SEQ ID NO: 2.

There are numerous *E. coli* expression vectors known to one of ordinary skill in the art useful for the expression of the antigen. Other microbial hosts suitable for use include bacilli, such as *Bacillus subtilis,* and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast. Efficient post translational glycosolation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector RNA in transformed cells can be confirmed by Southern analysis and production of a cDNA or opposite strand RNA corresponding to the antigen coding sequence can be confirmed by Northern analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Alternative vectors for the expression of antigen in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acid in mammalian cells (such as COS7).

The nucleic acid sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired nucleic acid sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Purified Antibodies

A purified antibody selectively reactive with the new virus of the present invention is also provided. The antibodies can be polyclonal or monoclonal. The antibodies can be selectively reactive with a unique epitope of the virus or a viral antigen. The term "reactive" means capable of binding or otherwise associating nonrandomly with an antigen. "Selectively reactive" as used herein describes an antibody or other ligand that does not cross react substantially with any virus or viral antigen other than the one specified, in this case, the new virus of the present invention. Antibodies can be made by many well-known methods (see also, Harlow and Lane, *Antibodies; A Laboratory Manual*, Cold Spring Harbor Laboratory, Cold Spring Harbor, N.Y., (1988)). Briefly, purified virus or viral antigen can be injected into an animal in an amount and in intervals sufficient to elicit an immune response. Antibodies can either be purified directly, or spleen cells can be obtained from the animal. The cells are then fused with an immortal cell line and screened for antibody secretion. The antibodies can be used to screen nucleic acid clone libraries for cells secreting the antigen. Those positive clones can then be sequenced as described in the Examples or by other methods (see, for example, Kelly et al., *Bio/Technology,* 10:163–167 (1992); Bebbington et al., *Bio/Technology,* 10:169–175 (1992)).

The antibody can be bound to a substrate or labeled with a detectable moiety or both bound and labeled. The detectable moieties contemplated with the composition of the present invention are those listed below in the description of the diagnostic methods, including fluorescent, enzymatic and radioactive markers.

Antigen Bound to Substrate

A purified virus or antigen of the new virus bound to a substrate and a ligand specifically reactive with the virus or viral antigen are also contemplated. Such a purified ligand specifically reactive with the virus or viral antigen can be an antibody. The antibody can be a monoclonal antibody obtained by standard methods and as described herein.

Serological Detection (Diagnosis) Methods Detecting Antibody with Antigen

The present invention also contemplates a method of detecting the presence of the new virus in a subject, comprising the steps of contacting an antibody-containing sample from the subject with a detectable amount of the virus or an antigenic polypeptide fragment of the virus and detecting the reaction of the fragment and the antibody, the reaction indicating the presence of the new virus.

Detecting Antigen with Antibody/Ligand

One example of the method of detecting the new virus of the present invention is performed by contacting a fluid or tissue sample from the subject with an amount of a purified antibody specifically reactive with the antigen as defined herein, and detecting the reaction of the ligand with the antigen. It is contemplated that the antigen will be on intact cells containing the antigen, or will be fragments of the antigen. As contemplated herein, the antibody includes any ligand which binds the antigen, for example, an intact antibody, a fragment of an antibody or another reagent that has reactivity with the antigen. The fluid sample of this method can comprise any body fluid which would contain the antigen or a cell containing the antigen, such as blood, plasma, serum, saliva and urine. Other possible examples of body fluids include sputum, mucus, gastric juice and the like.

ELISA

Enzyme immunoassays such as immunofluorescence assays (IFA), enzyme linked immunosorbent assays (ELISA) and immunoblotting can be readily adapted to accomplish the detection of the antigen. An ELISA method effective for the detection of the antigen can, for example, be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect antibody as well as antigen.

Competitive Inhibition Assay

Another immunologic technique that can be useful in the detection of the new virus or previous infection thereof utilizes monoclonal antibodies (MAbs) for detection of antibodies specifically reactive with antigen to the new virus. Briefly, sera or other body fluids from the subject is reacted with the antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition is a very specific test for a particular variety or strain since it is based on monoclonal antibody binding specificity. MAbs can also be used for detection directly in cells by IFA.

Micro-Agglutination Assay

A micro-agglutination test can also be used to detect the presence of antibodies in a subject. Briefly, latex beads (or red blood cells) are coated with the antigen and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or by spectrophotometer. In a modification of the above test, antibodies specifically reactive with the antigen can be bound to the beads and antigen in the tissue or body fluid thereby detected.

Sandwich Assay/Flow Cytometry/Immunoprecipitation

In addition, as in a typical sandwich assay, the antibody can be bound to a substrate and reacted with the antigen. Thereafter, a secondary labeled antibody is bound to epitopes not recognized by the first antibody and the secondary antibody is detected. Since the present invention provides antigen from the new virus for the detection of infection or convalescent exposure other serological methods such as flow cytometry and immunoprecipitation can also be used as detection methods.

In the diagnostic methods taught herein, the antigen can be bound to a substrate and contacted by a fluid sample such as serum, urine, saliva or gastric juice. This sample can be taken directly from the patient or in a partially purified form. In this manner, antibodies specific for the antigen (the primary antibody) will specifically react with the bound antigen. Thereafter, a secondary antibody bound to, or labeled with, a detectable moiety can be added to enhance the detection of the primary antibody. Generally, the secondary antibody or other ligand which is reactive, either specifically with a different epitope of the antigen or nonspecifically with the ligand or reacted antibody, will be selected for its ability to react with multiple sites on the primary antibody. Thus, for example, several molecules of the secondary antibody can react with each primary antibody, making the primary antibody more detectable.

Detectable Moieties

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, 1988).

Vaccines

The virus or viral antigen, e.g., a purified antigenic polypeptide fragment encoded by the nucleic acids of this invention can be used in the construction of a vaccine comprising an immunogenic amount of the antigen and a pharmaceutically acceptable carrier. The vaccine can be the entire antigen, the antigen on the intact new virus, *E. coli* or other strain, or an epitope specific to the antigen. The vaccine can also be potentially cross-reactive with antibodies to other antigens. The vaccine can then be used in a method of preventing infection with the new virus described herein.

Immunogenic amounts of the antigen can be determined using standard procedures. Briefly, various concentrations of a putative specific immunoreactive epitope are prepared, administered to a subject and the immunological response (e.g., the production of antibodies) of the subject to each concentration is determined.

The pharmaceutically acceptable carrier contemplated herein can comprise saline or other suitable carriers (Arnon, R. (Ed.) *Synthetic Vaccines* 1:83–92, CRC Press, Inc., Boca Raton, Fla., (1987)). An adjuvant can also be a part of the carrier of the vaccine, in which case it can be selected by standard criteria based on the antigen used, the mode of administration and the subject (Amon, R. (Ed.), 1987). Methods of administration can be by oral or sublingual means, or by injection, depending on the particular vaccine used and the subject to whom it is administered.

It can be appreciated from the above that the vaccine can be used as a prophylactic or a therapeutic modality. Thus, the invention contemplates methods of preventing or treating infection from the new virus and the associated ARDS diseases by administering the vaccine to a subject.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A purified polypeptide encoded by the nucleotide sequence identified as SEQ ID NO:1.

2. A purified polypeptide encoded by the nucleotide sequence identified as SEQ ID NO:2.

* * * * *